United States Patent [19]

Branham et al.

[11] Patent Number: 6,080,404
[45] Date of Patent: Jun. 27, 2000

[54] MATERIALS AND METHODS FOR REMOVAL OF SUBSTANCES FROM FLUIDS

[75] Inventors: Michael Lee Branham; Ian Ronald Tebbett; Edward Allan Ross, all of Gainesville, Fla.

[73] Assignee: University of Florida, Gainesville, Fla.

[21] Appl. No.: 08/924,689

[22] Filed: Sep. 5, 1997

[51] Int. Cl.⁷ .......................... A61K 39/00; B01D 15/04; G01N 33/53; C12N 11/06
[52] U.S. Cl. .................. 424/140.1; 210/660; 210/690; 210/691; 435/7.1; 435/7.8; 435/181; 528/403; 530/413; 604/5; 604/6
[58] Field of Search ............................. 530/413; 528/403; 435/7.1, 7.8, 181; 424/140.1; 604/5, 6; 210/660, 690, 691

[56] References Cited

U.S. PATENT DOCUMENTS 4,801,449  1/1989  Balint, Jr. et al. .
5,122,112  6/1992  Jones .
5,468,606  11/1995  Bogart ........................................ 435/5

OTHER PUBLICATIONS

Nakamura, R.M. and Tan, E.M. Recent progress in the study of autoantibodies to nuclear antigens. Human Pathology 9(1):86–91, Jan. 1978.

*Primary Examiner*—David Saunders
*Assistant Examiner*—Mary Beth Tung
*Attorney, Agent, or Firm*—Saliwanchik, Lloyd & Saliwanchik

[57] ABSTRACT

The subject invention concerns novel means for adsorption of materials from fluids. In a specific example, polymer substrates are modified with dendrimers to facilitate attachment of multiple ligands held at a distance from the surface of the substrate.

11 Claims, No Drawings

MATERIALS AND METHODS FOR REMOVAL OF SUBSTANCES FROM FLUIDS

BACKGROUND OF THE INVENTION

There are many instances in which it is desirable to remove substances from fluids. Particularly in the case of biological fluids it is possible to treat certain pathological conditions by removing detrimental substances from the blood. For example, extracorporeal immunoadsorption has been implemented as a strategy for the removal of disease-associated molecules from the blood of patients. This methodology has the potential to provide therapeutic benefit in a variety of contexts including the treatment of rheumatoid arthritis, mysethenia gravis, systemic lupus erythematosus (SLE), poisonings, overdose, cancer, amyloidosis and AIDS. This approach can be very useful due to its potential for highly specific removal of a target substance. Also, this approach has the potential to be more cost effective than classical drug discovery and is often the only therapeutic option in medical emergencies or in the terminally ill.

Several of the pathological conditions for which extracorporeal immunoadsorption has potential for providing therapeutic benefit are autoimmune conditions. These conditions are characterized by an abnormal immune response directed against normal autologous (self) tissues. Autoimmune diseases afflict huge numbers of individuals throughout the world. Known autoimmune disorders include diabetes mellitus, multiple sclerosis, autoimmune uveitis, rheumatoid arthritis, Addison's disease, thyroiditis, atrophic gastritis, myasthenia gravis, idiopathic thrombocytopenic purpura, hemolytic anemia, SLE, primary biliary cirrhosis, Wegener's granulomatosis, polyarteritisnodosa, and inflammatory bowel disease.

In certain autoimmune diseases, specific elements of the immune system predominate in mediating the pathogenic process, while in other autoimmune diseases, all of the components of the immune system combine to produce disease. Often, the abnormal immune response involves the presence in a patient's blood of antibodies which are part of the inappropriate self-destructive immune response. Antibodies are considered to play the major causal roles in diseases such as SLE, myasthenia gravis and Graves' disease.

A number of strategies have been used or proposed to suppress autoimmune diseases, most notably drugs, such as cyclophosphamide, cyclosporin A, methotrexate, and azathioprine. Steroid compounds, such as prednisone and methylprednisolone, are also employed in many instances. These drugs have limited long term efficacy against both cell- and antibody-mediated autoimmune diseases. Use of such drugs is limited because of their toxic side effects which include "global" immunosuppression. Prolonged treatment with these drugs inhibits the normal protective immune response to pathogenic microorganisms, thereby increasing the risk of infections. A further drawback is that immune-mediated elimination of aberrant cells is impaired and there is, this, an increased risk that malignancies will develop in patients receiving prolonged global immunosuppression.

Specifically exemplified herein is a new and advantageous treatment for autoimmune conditions. One autoimmune condition which can be treated according to the subject invention is SLE. It is well known that antibodies to histones are associated with SLE. Histones have a high affinity for glomerular basement membrane, such that when deposited onto it, they mediate the subsequent binding of immune complexes that form nephritic lesions. Direct evidence has shown that histones and anti-histone antibodies are present in the glomerular immune deposits of lupus-prone mice, as well as, in the renal biopsy of patients with SLE. There is a great need for an efficient and safe means for removing anti-histone antibodies producing an immediate benefit to the patient, as well as a long term benefit by activating B-cells which can then be eliminated by cytotoxic therapy.

The ability to accomplish extracorporeal removal of certain components from bodily fluids without increased risks to the patient has been established. Extracorporeal devices, such as kidney dialysis machines, are known in the art and have been shown to be therapeutically effective in eliminating abnormally high concentrations of certain components of serum. U.S. Pat. No. 4,801,449 which issued to Balint, Jr. et al. discloses an immunoadsorbentmaterial comprising Protein A for removing IgG from biological fluids as a method for treating Kaposi's sarcoma. U.S. Pat. No. 5,122,112, which issued to Jones teaches a method for treating antigen-related disease by identifying the predominant antigen associated with the disease and then using an antigen-specific immunoadsorbent to remove the antigen from a patient's system.

There remains a need for improving the efficiency of methods for extracorporeal treatment of blood. There is also a need for methods of removing constituents from other fluids.

BRIEF SUMMARY OF THE INVENTION

The subject invention provides materials and methods for removing substances from fluids. Fluids from which target materials can be adsorbed by the system of the subject invention include, but are not limited to, whole blood and other biological fluids, and environmental samples. In a preferred embodiment, the substances to be removed from the fluid are proteins or other molecules present in biological fluids. In one embodiment, the subject invention provides materials and methods for the removal of unwanted molecules from whole blood. These unwanted molecules may be, for example, antigens or antibodies associated with pathological conditions. Advantageously, these molecules can be removed in a highly specific manner.

Thus, the subject invention provides a system whereby a wide variety of molecules can be selectively and efficiently removed from fluids. This is accomplished by immobilizing ligands, utilizing advantageous linker molecules (which alter the surface/fluid interaction), to a surface over which a fluid is passed.

In a specific embodiment of the subject invention, the removal of substances from blood is accomplished by contacting whole blood with chemically derivatized dialysis fibers, or other fibers with substantially equivalent chemical and physical properties. These fibers have been modified so that ligand molecules which remove unwanted constituents from the blood are indirectly attached to the surface of the fiber. The attachment of the ligands is indirect in that the ligands which remove the unwanted constituents are attached to a polymer which is itself attached to the fiber surface.

Thus, one aspect of the subject invention pertains to surface-modified hollow-fiber substrates which are useful for the immunoadsorption of constituents from fluids. Hollow-fiber substrates have been modified so that ligands are presented above the surface of the substrate in a manner which provides a high degree of contact between the ligands and a fluid which passes over, or around, the substrate. In a preferred embodiment, the ligand is attached to a polymer which is then attached to the surface of the substrate. Preferably, the polymer is a "star polymer" which has multiple sites at which ligands may be attached. The star polymer extends outwardly from the surface of the substrate so as to allow the multiple ligands to be effectively exposed to fluid which passes over or around the surface of the substrate. The ligands may be designed to bind with any of a variety of constituents which may be in the fluid. The ligand may be highly specific such as a receptor for a particular protein or the ligand may be less specific such as a protein which will bind with a class of antibodies.

In one embodiment which is specifically exemplified herein, the immunoadsorption system of the subject invention can be used to remove anti-histone antibodies from blood as a therapy for systemic lupus erythematosus (SLE). Using an extracorporeal circuit it has been found that histones immobilized onto the surface of hollow-fiber dialyzers provide an efficient method for the ex vivo extraction of anti-histone antibodies. Advantageously, the system of the subject invention can be used to remove constituents from either whole blood or plasma thereby simplifying and expediting the process.

One aspect of the subject invention pertains to the procedures which can be used to chemically modify substrate surfaces. The methods of the subject invention can be used to prepare immunoadsorption devices from commercially available materials such as, for example, hollow-fiber dialyzers. Other chemically-modified materials, as disclosed herein, can be used for adsorption of target materials from various fluids. The substrate to be modified would typically be a polymer and can be in the form of a tube, fiber, plate, membrane, sheet, particle or sphere or other shape which can be readily contacted with a fluid.

The advantages of using the modified dialyzers and other substrate surfaces of the subject invention include: 1) the starting materials are safe, designed for human use and are commercially available; 2) these devices allow for the adsorption of a variety of blood-borne antigens without prior plasma separation; 3) the components are sterilizable, inexpensive, and may be reused; 4) dialyzer and other surface modification can be individualized for the specific needs of the application on short notice; and 5) dialyzers are already constructed to have a high surface area.

DETAILED DISCLOSURE OF THE INVENTION

The subject invention provides materials and methods useful in the efficient removal of substances from fluids. The fluids from which substances can be removed utilizing the methods of the subject invention include, but are not limited to biological fluids and environmental samples. Specifically exemplified herein is the removal of constituents from blood.

The high efficiency of the removal process of the subject invention arises from the use of unique immobilization technology whereby star polymers are attached to a surface by one arm of the star polymer and ligands are attached to the remaining arms of the star polymer. This arrangement effectively increases the number of ligands to which the fluid is exposed as the fluid passes over the substrate. In a preferred embodiment, the star polymers are attached such that the ligands are presented at a distance away from the surface such that fluid may effectively flow around the star polymer thereby increasing the contact between the fluid and the ligands. It has been found that the system of the subject invention advantageously provides a high level of contact between the fluid and the ligands thereby enhancing the removal of the substance of interest. The system of the subject invention is particularly advantageous because molecules can be effectively removed from whole blood thereby making it unnecessary to process the blood prior to performing the immunoadsorption procedures.

The subject invention is useful not only for effectively removing unwanted substances from the blood of a patient, but also the techniques of the subject invention can be used to efficiently isolate desired substances from biological fluids and other fluid samples. The desired substances will bind to molecules attached to the star polymer and then can be released and recovered. The release of the desired compounds can be achieved in a variety of ways known to those skilled in the art including, for example, changing the salt concentration of the fluid which surrounds and passes over the star polymer.

In one embodiment the star polymer used according to the subject invention is star 407-PEG (polyethylene glycol) which has a total of 64 polymer arms. One of the 64 arms is attached to the solid substrate thereby leaving 63 arms available for attachment of ligands. Other "star" polymers (e.g., dendrimers) can be used in the system of the subject invention. However, polyethylene glycol is particularly preferred because of its surface hydrophilizing and histocompatibilityadvantages. As used herein, "star polymers" refer to polymers having multiple sites to which ligands may be attached.

One aspect of the subject invention pertains to methods for attaching the star polymer to the solid substrate. In a preferred embodiment the solid substrate is dialyzer hollow fibers. The dialysis hollow fibers can be any standard polymeric dialysis hollow fiber including, for example, polymethylmethacrylate (PMMA) or polysulfone (PS) hollow fibers. Other substrates can also be used. The star polymer can be attached to the surface of, for example, a polysulfone or a cellulose acetate material. The material to which the polymers are attached may be, for example, hollow fibers, films, plates, sheets, membranes, particles, or spheres.

A further aspect of the subject invention pertains to methods for attaching ligands to the star polymer. Specifically exemplified herein is the attachment of histones to a tresylated star-PEG polymer. The histones can be attached to the star polymer through terminal lysine residues of the histone. Specifically, the histone can be attached at the terminal amine of lysine. Advantageously, the attachment of ligands to the star polymer according to the subject invention does not destroy the three dimensional configuration of the ligand and, therefore, the ligand is able to efficiently bind with the substance to be removed from the fluid. A major advantage of using star-PEG technology is that the immobilized ligands are raised above the surface of the dialyzer surface on one of as many as 64 arms. This configuration results in a greatly increased surface area compared to a chemically modified dialyzer in which the ligand is bound directly to the surface of the support material.

The system of the subject invention can be used in a wide variety of settings wherein it is desired to remove a substance from a fluid. Reference herein to "removal" of a substance refers in a broad sense to actual physical removal as well as to transformation of the substance to another form. Thus, in one embodiment of the subject invention, enzymes can be attached to the substrate such that, when exposed to the fluid sample, these enzymes will act upon constituents in the fluid thereby converting these constituents to a different form. In a specific embodiment these enzymes may be, for example, liver or pancreatic enzymes which detoxify blood constituents. Alternatively, such biological conversion can be used according to the subject invention to remediate environmental samples.

In a further embodiment of the subject invention, immobilized microsomal enzymes can be used to study the metabolism of new pharmaceutical compounds in a physiologically controlled environment. In another embodiment of the subject invention, immobilized self-antigens can be used to study the adsorption of autoantibodies or other disease associated antigens. In a specific embodiment, this antigen may be a histone and the histone can be used to remove anti-histone autoantibodies from blood.

A further embodiment of the subject invention pertains to cell culture supernatant fractionation wherein products of cellular metabolism and gene expression can be monitored and separated on-line with elution of the product.

In a further embodiment of the subject invention, targeting of therapeutic molecules such as radioimmunoconjugates to selected tissue-types can be improved by removing extraneous circulating molecules. For example, after a radioimmunoconjugate has been administered to a patient and has accumulated at a target tissue, the immunoadsorption system of the subject invention can be used to adsorb unbound circulating radioimmunoconjugate. This can be readily accomplished using biotinylated monoclonal antibodies as the therapeutic agent and modifying the substrate surface of the subject invention to present avidin molecules.

In a further embodiment, the modified surfaces of the subject invention can be used as a substrate to grow cells. Advantageously, although the cells are anchored to the surface via the polymer, they are suspended above the surface facilitating enhanced exposure of the cells to the surrounding medium. The cells may be attached to the polymer through, for example, a ligand which attaches to a cell surface molecule.

The modified surfaces of the subject invention can also be used in diagnostic procedures wherein it is desired to detect an analyte of interest in a fluid sample. Using the modified surfaces of the subject invention it is possible to increase the sensitivity of these assays by effectively exposing large numbers of ligands above the substrate surface thereby enhancing the contact between the fluid and the ligands.

Following is an example which illustrates procedures for practicing the invention. This example should not be construed as limiting. All percentages are by weight and all solvent mixture proportions are by volume unless otherwise noted.

EXAMPLE 1

Preparation and Use of Modified Dialyzers

The preparation of chemically modified dialyzers of the invention can proceed in three steps as follows:

(1) Activation of the PMMA hollow-fibers with 690 ug hour per $cm^2$ PMMA hydrazine monohydrate in 50% MeOH;

(2) Coupling of tresylated star 407-PEG onto the hydrazido-amine to form the hydrophilized membrane surface; and (3) Immobilizing the lysine-rich fraction of histone onto these Star polymers via coupling reaction between the tresyl end groups (63 per Star) and the terminal amine on lysine residues of the histones.

The non-specific binding sites are then taken up by incubating the modified dialyzers in 0.1% albumin PBS.

In a procedure to show efficacy, anti-histone antibodies were extracted from saline solutions and plasma by perfusion through these devices for 4 hours. It was found that in vitro clearance of human anti-histone antibodies (AHA) in the device was equal to 13.6 mg AHA per $m^2$ of modified membrane.

EXAMPLE 2

Preparation of Modified Polysulfone Surfaces

Polysulfone surfaces, such as hollow fibers or film can be activated by nitration (nitronium tetrafluoroborate in sulfane/acetonitrile). The nitrated aryl linkages in the chain can then be reduced to the corresponding amine ($NO_2$ to $NH_2$) using chromous chloride ($CrCl_2$) in dilute HCl. Tresylated star-PEGs can then be coupled to the aminated surface by reactions identical to that in the PMMA modification with subsequent protein immobilization. The absorption capacity for the modified polysulfone surfaces have been determined to be 29.3 mg AHA per $m^2$.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for the extracorporeal treatment of a pathological condition comprising removing a substance from a fluid wherein said method comprises passing said fluid over a material wherein said material comprises a solid substrate to which is attached a dendrimer, having multiple ligand attachment sites, such that the ligand attachment sites of the said dendrimer are presented above the surface of said substrate, and wherein a ligand is attached to said dendrimer.

2. The method, according to claim 1, wherein said fluid is whole blood.

3. The method, according to claim 1, wherein said substance removed from the fluid is selected from the group consisting of antigens, antibodies, and toxins.

4. The method, according to claim 3, wherein anti-histone antibodies are removed from said fluid.

5. The method, according to claim 1, wherein an enzyme is attached to said dendrimer.

6. A method for purifying a fluid known to contain a substance, wherein said method comprises passing said fluid over a solid substrate to which is attached a dendrimer, having multiple ligands which remove said substance from said fluid; and wherein said fluid is selected from the group consisting of biological fluids and environmental samples.

7. The method, according to claim 6, wherein said substrate is tubing and wherein said dendrimers are attached to the inside of said tubing and said fluid flows through said tubing thereby contacting said dendrimers and attached ligands.

8. The method, according to claim 7, wherein said fluid recirculates through said tubing.

9. The method, according to claim 7, wherein said tubing is dialysis tubing.

10. The method, according to claim 6, wherein the removed substance is released and recovered from said dendrimers.

11. The method, according to claim 6, wherein said method is capable of removing 13.6 mg/$m^2$ of substance.

* * * * *